(12) United States Patent
Kopp et al.

(10) Patent No.: US 7,993,647 B2
(45) Date of Patent: Aug. 9, 2011

(54) MONOCLONAL ANTIBODIES TO HIV-1 AND METHODS OF USING SAME

(75) Inventors: Jeffrey B. Kopp, Bethesda, MD (US); Terence M. Phillips, Washington, DC (US); Ulrich Schubert, Jena/Thuringen (DE); John Yewdell, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 236 days.

(21) Appl. No.: 11/630,880

(22) PCT Filed: Jun. 22, 2005

(86) PCT No.: PCT/US2005/022135
§ 371 (c)(1), (2), (4) Date: Jan. 10, 2008

(87) PCT Pub. No.: WO2006/007471
PCT Pub. Date: Jan. 19, 2006

(65) Prior Publication Data
US 2008/0293036 A1 Nov. 27, 2008

Related U.S. Application Data

(60) Provisional application No. 60/585,282, filed on Jul. 1, 2004.

(51) Int. Cl.
*A61K 39/42* (2006.01)
*C12P 21/08* (2006.01)
*C07K 16/00* (2006.01)
*G01N 33/53* (2006.01)

(52) U.S. Cl. ............... 424/148.1; 424/130.1; 530/387.3; 530/388.8; 530/388.1; 530/388.15; 435/7.1

(58) Field of Classification Search .................. None
See application file for complete search history.

(56) References Cited

U.S. PATENT DOCUMENTS
5,780,220 A 7/1998 Weiner et al.

FOREIGN PATENT DOCUMENTS
| EP | 0 403 333 A2 | 12/1990 |
| EP | 0 403 333 A3 | 12/1990 |
| WO | WO 03/089472 A2 | 10/2003 |
| WO | WO 03/089472 A3 | 10/2003 |

OTHER PUBLICATIONS

Kashmiri S. et al. "SDR grafting—a new approach to antibody humanization". Methods. May 2005;36(1):25-34.*
Tamura M. et al "Structural correlates of an anticarcinoma antibody: identification of specificity-determining residues (SDRs) and development of a minimally immunogenic antibody variant by retention of SDRs only". J Immunol. Feb. 1, 2000;164(3):1432-41.*
Kashmiri S. "SDR grafting—a new approach to antibody humanization" Methods 36 (2005) 25-34.*
Presta, LG "Engineering Antibodies for Therapy" Current Pharmaceutical Biotechnology, 2002, 3, 237-256 237.*
Köhler G, Milstein C. "Continuous cultures of fused cells secreting antibody of predefined specificity. 1975" J Immunol. Mar. 1, 2005;174(5):2453-5. (Reprinted with permission from Nature 256 (5517): 495-497 (1975).*
Levy, David, et al. "Serum Vpr regulates productive infection and latency of human immunodeficiency virus type 1," Proc. Natl. Acad. Sci., 1994, vol. 91, pp. 10873-10877. XP-002345842.

* cited by examiner

*Primary Examiner* — Bo Peng
(74) *Attorney, Agent, or Firm* — Townsend and Townsend and Crew, LLP; Siegfried J.W. Ruppert (57) ABSTRACT

The present invention provides monoclonal antibodies to HIV-1 Vpr and hybridoma cell lines that produce the monoclonal antibodies to HIV-1 Vpr. Methods for use of such antibodies in the detection of HIV-1 infection are also provided.

29 Claims, 1 Drawing Sheet

MONOCLONAL ANTIBODIES TO HIV-1 AND METHODS OF USING SAME

CROSS-REFERENCES TO RELATED APPLICATIONS

This application is a U.S. National Phase of PCT/US05/022135, filed on Jun 22, 2005, which claims the benefit of U.S. Provisional Application No. 60/585,282, filed Jul. 1, 2004, the disclosures of which are incorporated by reference in their entirety for all purposes.

BACKGROUND OF THE INVENTION

The human immunodeficiency virus (HIV) is the cause of acquired immune deficiency syndrome (AIDS) (Barre-Sinoussi, F., et al., 1983, Science 220:868-870; Gallo, R., et al., 1984, Science 224:500-503). AIDS first appeared in a single individual in the early 1980's, and has now become a worldwide pandemic. By the end of 2002, nearly 42 million people were infected, and since the start of the epidemic, more than 22 million people have died. Thus, the current global HIV pandemic ranks among the greatest infectious disease scourges in human history.

HIV transmission readily occurs through exposure of the oral, rectal, or vaginal mucosa to the virus during sex, by inoculation with contaminated blood products, through the use of contaminated equipment during injection drug use, by maternal circulation, or by breast feeding. Sexual transmission accounts for more than 90% of the world wide infections. As a result, individuals in their most productive years of life are overrepresented in the population of infected, disabled, and dying individuals, and this gives rise to enormous economic, and social consequences.

Spread of the disease is facilitated by the long latency period of the virus. Since individuals with HIV infections can be asymptomatic for many years before they develop severe immunodeficiency (AIDS), these infected, asymptomatic individuals can unknowingly transmit the virus to many sexual partners over the years.

Unfortunately, there is still no effective vaccine to protect individuals against infection with HIV, nor is there a cure for HIV-1 infection. The virus's ability to replicate within the host immune cells and the high rate of mutation and genomic evolution combine to make vaccine development difficult, and the ability of the virus to "hide" within the nervous system where it is hard for drugs to penetrate, has so far made a cure impossible.

Complications of HIV-1 infection and acquired immunodeficiency syndrome are a primary cause of morbidity and mortality associated with HIV-1 infection, and significantly reduce the quality of life for people living with AIDS. Although the exact mechanism by which the virus causes complications is not completely understood, it is known that some complications are related to the immune deficiency, whereas others are a secondary consequence of infection with the virus itself.

It has been proposed that some of the complications of HIV-1 infection may be due to HIV-1 proteins acting on infected cells or bystander cells. Certain HIV-1 proteins, such as Tat and Vpr, may enter cells via non-receptor mechanisms to influence cell function and possibly to effect changes that lead to some of the complications that are a consequence of infection with the virus itself. HIV-1 proteins that influence the development of complications through their action on infected cells or bystander cells may derive from virions that undergo degradation or lysis, or as proteins released by infected cells. Whatever their origin, these proteins may be present within extracellular fluid or in plasma.

Immunoassays for the routine detection of HIV-1 infection are known in the art. HIV-1 disease progression can be routinely monitored by measuring the number of circulating CD4 lymphocytes and the quantity of viral RNA in the blood. Alternatively, progression can be monitored by measuring the HIV-1 Gag protein p24 in biologic samples, though this may be less accurate gauge of viral activity than measurements of viral RNA. However, to date there is no clinical assay to detect, or diagnose the complications of HIV-1 that may derive from HIV-1 proteins acting on infected cells or bystander cells.

If the hypothesis that the level of one or more of the regulatory or accessory proteins, e.g. Vpr, correlates with one or more of the complications of HIV-1 infections, then the measurement of these proteins in biologic fluids may be important in the diagnosis and management of HIV-1 complications. Early diagnosis of HIV-1 complications would permit a patient to make decisions about management of their disease that may ultimately improve their quality of life and their ability to live with the disease.

Clearly then, what is needed is a means by which complications of HIV-1 can be routinely detected, diagnosed, and monitored. The invention disclosed herein addresses these and other needs.

SUMMARY OF THE INVENTION

The HIV pandemic is a continuing problem worldwide. Indeed, the epidemic is already responsible for more deaths than bubonic plague, and by the end of 2001, will have overtaken "Spanish influenza" as most deadly epidemic in human history. There is no vaccine effective to prevent the spread of HIV-1, and there is no cure for the acquired immune deficiency syndrome that results from HIV-1 infection. Therefore, for the foreseeable future, reliable, sensitive systems for the detection of HIV-1 infected individuals will remain the best defense in the fight against HIV-1 infection and AIDS.

HIV-1 infection is routinely diagnosed by various immunoassays that detect the presence of anti-HIV antibodies in body fluids (e.g., blood, saliva, or urine). HIV-1 progression is routinely monitored by measuring the number of circulating CD4 lymphocytes and the quantity of viral RNA in the blood. However, to date, there has been no clinical assay to measure the level of HIV-1 regulatory or accessory proteins in biologic fluids. If the hypothesis that the level of one of these proteins, e.g. Vpr, correlates with one or more of the complications of HIV-1 infections, then the measurement of these proteins may be important in the diagnosis and management of these complications.

In a first aspect, the invention provides an antibody that competitively inhibits binding to HIV-1 viral protein R of a second antibody produced by hybridoma cell lines selected from the group consisting of hybridoma cell line 9F12 and 10F2 (American Type Culture Collection patent deposit numbers PTA-5560 and PTA-5561, deposited on Oct. 2, 2003, ATCC, Manassas, Va., 20110). In one embodiment, the antibody is monoclonal. In another embodiment, the antibody is a chimeric antibody and in another embodiment the antibody is a humanized antibody. In a related embodiment, the antibody is conjugated to a detectable label.

The invention also provides an isolated hybridoma cell line selected from the group consisting of hybridoma cell line 9F12 and 10F2 (American Type Culture Collection patent deposit numbers PTA-5560 and PTA-5561).

The invention also provides a method for detection of HIV-1 viral protein R that comprises contacting a sample with a first antibody that competitively inhibits binding to HIV-1 viral protein R of a second antibody produced by hybridoma cell lines selected from the group consisting of hybridoma cell line 9F12 and 10F2 (American Type Culture Collection patent deposit numbers PTA-5560 and PTA-5561), and detecting the antibody-antigen complex in the sample. In a related embodiment, the method for detection of HIV-1 viral protein R further comprises quantitating the amount of antibody-antigen complex to determine the amount of HIV-1 viral protein R in the sample. In related embodiments, the sample is a sample of a biologic fluid and the biologic fluid is selected from the group consisting of serum and plasma. In one embodiment, the first antibody is detectably labeled. In another embodiment, the method of detection is capillary electrophoresis. In still another embodiment the method of detection is immunoaffinity capillary electrophoresis. In one embodiment, the method for detection of HIV-1 viral protein R further comprises comparing the amount of HIV-1 viral protein R in the sample to a standardized control to determine disease progression or the presence of particular complications such as such as neuropathy, dementia, metabolic syndrome, or nephropathy.

Other aspects, objects and advantages of the present invention will be apparent from the detailed description that follows.

DETAILED DESCRIPTION OF THE INVENTION

I. Definitions

The terms "HIV-1 viral protein R," "HIV-1 Vpr" and "Vpr" refer to a small approximately 14K kDa, 96 amino acid accessory protein encoded by the Human immunodeficiency virus type 1 (HIV-1) R gene (Wong-Staal, F., et al., (1987) AIDS Res. Hum. Retroviruses 3:33-39).

The term "antibody" refers to a polypeptide encoded by an immunoglobulin gene, or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Examples of antibody functional fragments include, but are not limited to, complete antibody molecules, antibody fragments, such as Fv, single chain Fv (scFv), complementarity determining regions (CDRs), $V_L$ (light chain variable region), $V_H$ (heavy chain variable region), Fab, F(ab)2' and any combination of those or any other functional portion of an immunoglobulin peptide capable of binding to target antigen (see, e.g., Fundamental Immunology (Paul ed., 3d ed. 1993). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al, Nature 348:552-554 (1990)). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al (1996) *Cancer Res.* 56:3055, Adams et al. (1993) *Cancer Res.* 53:4026, and McCartney, et al. (1995) *Protein Eng.* 8:301.

References to "$V_H$" or a "VH" refer to the variable region of an immunoglobulin heavy chain, including an Fv, scFv, a disulfide-stabilized $F_V$(dsFv) or Fab. References to "$V_L$" or a "VL" refer to the variable region of an immunoglobulin light chain, including of an Fv, scFv, dsFv or Fab.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. The numbering of the light and heavy chain variable regions described herein is in accordance with Kabat (see, e.g., Johnson et al., (2001) "Kabat Database and its applications: future directions" *Nucleic Acids Research,* 29: 205-206; and the Kabat Database of Sequences of Proteins of Immunological Interest, Feb. 22, 2002 Dataset).

The positions of the CDRs and framework regions are determined using various well known definitions in the art, e.g., Kabat, Chothia, international ImMunoGeneTics database (IMGT), and AbM (see, e.g., Johnson et al., supra; Chothia and Lesk, *J. Mol. Biol.* 196:901-917 (1987); Chothia et al., *Nature* 342, 877-883 (1989); Chothia et al., *J. Mol. Biol.* 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.,* 28: 219-221 (2000); and Lefranc, M.-P. IMGT, the international ImMunoGeneTics database. *Nucleic Acids Res.* 29(1):207-9 (2001); MacCallum et al., *J. Mol. Biol.,* 262 (5):732-745 (1996); and Martin et al, *PNAS USA* 86:9268-9272 (1989); Martin, et al, *Methods Enzymol.,* 203:121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

A "chimeric antibody" as used herein, refers to an antibody whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A therapeutic chimeric antibody thus comprises a hybrid protein that may be composed of, for example, the variable or antigen-binding domain from a mouse antibody and the constant or effector domain from a human antibody. Naturally, this example is not limiting. Combinations of variable and constant domains may involve mammalian species other than mouse and human as well.

The term "humanized antibody" refers to an immunoglobulin molecule comprising a human-like framework region and one or more CDR's from a non-human (usually a mouse or rat) immunoglobulin. Constant regions need not be present, but if they are, they must be substantially identical to human immunoglobulin constant regions, i.e., at least about 85-90%, preferably about 95% or more identical. The resultant humanized antibody is expected to bind to the same antigen as the donor antibody that provides the CDR's. Thus, used herein, the term "humanized antibody" is an embodiment of chimeric antibodies wherein substantially less than an intact human variable domain has been substituted by the corresponding sequence from a non-human species. In practice, humanized antibodies are typically human antibodies in which some CDR residues are substituted by residues from analogous sites in rodent antibodies.

The term "hybridoma cell line" refers to a permanent cell line derived from the fusion of a cultured a neoplastic lymphocyte (e.g. a mouse plasmacytoma cell) and specific antibody producing cell i.e. a primed B or T lymphocyte. All of the cells of a particular hybridoma cell line express the specific immune potential of the B or T lymphocyte. For example, a B cell hybridoma continuously secretes pure monoclonal antibody of a specificity determined by the immune potential of the parental B cell. Thus, such a cell line may be used for the large scale production of the specific antibodies produced by the B cell. Hybridoma cell lines are permanently adapted to growth in culture, but may also form specific antibody producing tumors in vivo.

The term "effector moiety" means the portion of an immunoconjugate intended to have an effect on a cell targeted by the targeting moiety or to identify the presence of the immunoconjugate. Thus, the effector moiety can be, for example, a therapeutic moiety, such as a cytotoxic agent or drug, or a detectable moiety, such as a fluorescent label.

The term "immunoconjugate" refers to a composition comprising an antibody linked to a second molecule such as a detectable label or effector molecule. Often, the antibody is linked to the second molecule by covalent linkage.

In the context of an immunoconjugate, a "detectable label" or "detectable moiety" refers to, a portion of the immunoconjugate which has a property rendering its presence detectable. For example, the immunoconjugate may be labeled with a radioactive isotope which permits cells in which the immunoconjugate is present to be detected in immunohistochemical assays. A "detectable label" or a "detectable moiety" is a composition detectable by spectroscopic, photochemical, biochemical, immunochemical, chemical, or other physical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins which can be made detectable, e.g., by incorporating a radiolabel into the peptide or used to detect antibodies specifically reactive with the peptide. An introduction to labels, labeling procedures, and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo (see Harlow & Lane, ANTIBODIES, A LABORATORY MANUAL, Cold Spring Harbor Press, New York (1988) and Harlow & Lane, USING ANTIBODIES, A LABORATORY MANUAL, Cold Spring Harbor Press, New York (1999), for a description of immunoassay formats and conditions that can be used to determine specific immunoreactivity). In some cases, the immunologically reactive conditions employed in the methods of the present invention may be "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The term "binding specificity," "specifically binds to an antibody" or "specifically immunoreactive with," when referring to an epitope, refers to a binding reaction which is determinative of the presence of the epitope in a heterogeneous population of proteins and other biologics. Thus, under designated immunoassay conditions, the specified antibodies bind to a particular epitope at least two times the background and more typically more than 10 to 100 times background. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate (see, e.g. Harlow & Lane, supra).

The phrase "antibodies that competitively inhibit binding to HIV-1 viral protein R of a second antibody produced by hybridoma cell lines selected from the group consisting of hybridoma cell line 9F12 and 10F2" refers to antibodies that are considered equivalent to the antibodies of the present invention. Antibodies that competitively inhibit binding of 9F12 and 10F2 antibodies to Vpr bind an epitope that is either the same as the epitope bound by the 9F12 and 10F2 antibodies or is a sterically overlapping epitope. Such antibodies can be identified by a competition assay.

A competition assay involving competition between a 9F12 or a 10F2 antibody and a test antibody might be conducted using, for example, an ELISA format as follows. HIV-1 Vpr protein may be affixed to a solid support such as a 96 well polystyrene plate. A solution comprising the unlabeled 9F12 or 10F2 antibody is added to the wells containing the affixed Vpr, and binding is allowed to take place. The excess unlabeled antibody is not removed by washing. A labeled test antibody is added to the test wells containing the unlabeled 9F12 or 10F2 antibody and is allowed to compete for binding of the affixed Vpr. If the labeled test antibody binds the same epitope as the unlabeled 9F12 or 10F2 antibody, the unlabeled 9F12 or 10F2 antibody will competitively inhibit binding of the labeled test antibody, and no label will be detected after the wells are washed at the completion of the binding assay. On the other hand, if the labeled test antibody binds a different epitope than the unlabeled 9F12 or 10F2 antibody, label will be detectable in the well at the completion of the binding assay. Competition binding assays are known in the art (see e.g., Harlow and Lane, *Using Antibodies, A Laboratory Manual* CSHLP (1999)).

It is understood that some of the antibodies that successfully challenge the binding of 9F12 or 10F2 antibodies may be antibodies that have conservative amino acid substitutions relative to the 9F12 and 10F2 antibodies. Such "conservatively modified variants" are in addition to and do not exclude polymorphic variants, interspecies homologues, and alleles of the invention.

Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

The expression "conservatively modified variants" and it equivalents applies to both nucleic acid and amino acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

The terms "identical" or percent "identity," in the context of two or more nucleic acid or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, 95%, 96%, 97%, 98%, or 99% identity over a specified region), when compared and aligned for maximum correspondence over a designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

While any method known in the art for making such determinations may be used, for the purpose of the present invention, the BLAST algorithm, described in Altschul et al., *J. Mol. Biol.* 215:403-410 (1990) and Karlin et al., *PNAS USA* 90:5873-5787 (1993), and incorporated herein by reference, may be used preferentially for determining sequence identity according to the methods of the invention. A particularly useful BLAST program is the WU-BLAST-2 program (Altschul et al., *Methods in Enzymology* 266: 460-480 (1996) also incorporated herein by reference). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A percent sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

A polypeptide is also considered to be substantially identical to a second polypeptide, for example, where the two peptides differ only by conservative substitutions. An indication that two nucleic acid sequences are substantially identical is that the two molecules or their complements hybridize to each other under stringent conditions, as described below. Another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The term "disease progression" is a relative term that refers to changes in the manifestation of a disease over time. The changes can be positive or negative. Measures of disease progression can be made by methods that assess changes in the titer of the virus, the stage of infection achieved by the virus (e.g., types of cells infected), the condition of the individual infected with the virus or any other diagnostic feature of the disease over time. "Complications of HIV-1 disease" or equivalent phrases such as "AIDS complications" or "complications associated with HIV-1 infection" refer to the morbid processes or events that occur during the course of a disease, but which are not an essential part of the disease itself. Complication may result from independent causes. For example, in the case of HIV-1 disease or AIDS, an individual may be subject to opportunistic infections by microorganisms that are not pathogenic to non-immune compromised individuals. Alternatively, complications may develop as a secondary consequence of infection with the virus itself. For example, the level and presence of certain regulatory and accessory proteins e.g., Tat and Vpr, may correlate with one or more complications of HIV-1 infection. Without being bound by theory, it is thought that these proteins may enter the extracellular fluid or plasma from virions that undergo degradation or lysis or as proteins released from infected cells. From the extracellular fluid or plasma the proteins may enter infected cells or bystander cells by non-receptor mechanisms and influence cell function. It has been proposed that some of the complications of HIV-1 infection may derive from the action of these proteins on cells.

Complications of HIV-1 infection may be manifest in a large variety of ways including, but not limited to neurological complications or "neuropathy." The term "neuropathy" as used herein refers to a disorder affecting any segment of the nervous system, and may be manifest in symptoms and syndromes including, but not limited to, demyelinating neuropathies, pain, dementia, memory disturbance, myopathy (muscle disease), seizure, tremor, weakness, spinal cord problems, gait disorder and falls, shingles and Bell's Palsy. Other complications of HIV-1 infection may include nephropathy which is a common cause of end-stage renal failure in seropositive patients or "metabolic syndrome" by which is meant a multi-dimensional syndrome that may involve, but which is not limited to the following: elevations of triglycerides and cholesterol, and resistance to insulin which can cause diabetes, weird body fat redistribution including but not limited to the appearance of buffalo hump, increased abdominal size, breasts, and visceral adipose tissue (VAT), and decreased fat in the face, arms, legs, and buttocks.

II. Introduction

In an exemplary embodiment, the present invention provides monoclonal antibodies to HIV-1 Vpr. These antibodies, as well as antibodies that competitively inhibit the binding of these antibodies to Vpr, can be used to detect Vpr in biological fluids such as plasma, serum or urine. Thus, in addition to monoclonal antibodies, the present invention also provides methods for detection of HIV-1 viral protein R. In one aspect, the method can be used to detect Vpr. In another aspect, the method for detection of HIV-1 viral protein R further comprises comparing the amount of HIV-1 viral protein R in the sample to a standardized control to determine disease progression, the presence or the likelihood of occurrence of particular complications such as neuropathy or metabolic syndrome.

HIV is a member of the lentivirus family of retroviruses (Teich, N., et al., 1984, RNA Tumor Viruses, Weiss, R., et al., eds., CSH-Press, pp. 949-956). In addition to encoding Gag, Pol and Env proteins that are common to all retroviruses, it also encodes regulatory and accessory proteins common to lentiviruses. One of these proteins is the multifunctional accessory protein, Viral protein R (Vpr).

Vpr functions early in infection, it is incorporated into the viral particle and may interact with cellular regulatory mechanisms important in the establishment of infection (Cohen et al., *J. Virol.* 64:3097-3099 (1990); Yu et al., *J. Virol.* 64:5688-5693 (1990); and, Yuan et al., *AIDS Res. Hum. Retroviruses* 6:1265-1271 (1990). Vpr is important for promoting the transport of the preintegration complex into the nucleus and induction of G2 host cell cycle arrest (Heinzinger, et al., *PNAS USA* 91:7311-7315 (1994); and Fletcher et al., *EMBO*, 15:6155-6165 (1996); Lu, et al., *J. Virol.* 67, 6542-6550 (1993); Mahalingam, et al., *Virology* 212:331-339 (1995); DiMarzio et. al., *J. Virol.* 69:7909-7916 (1995); Levy et al., *Cell* 72:541-550 (1993); Rogel et al., *J. Virol.* 69:882-888 (1995); Jowett et al., *J. Virol.,* 69:6304-6313 (1995); Mahalingam et al., *DNA Cell Biol.* 16:137-153 (1997)). Vpr also facilitates viral replication. Thus, Vpr functions throughout the viral life cycle and is therefore an ideal marker for the detection of HIV-1 at all stages of HIV-1 infection.

III. Production and Purification of HIV-1 Vpr Polypeptides

A. Producing HIV-1 Viral Protein R

To practice the methods of the invention, one of skill in the art must first acquire sufficient amounts of Vpr to immunize animals for the purpose of preparing antibodies. The HIV-1 Vpr proteins encompassed by the present invention can easily be designed and synthesized using DNA encoding the proteins as the starting material.

1. De Novo Synthesis of DNA Encoding HIV-1 Vpr.

One of skill in the art will recognize that HIV-1 Vpr and/or fragments thereof can be synthesized from DNA molecules that encode the HIV-1 Vpr polypeptides. Depending on the desired size and characteristics of the polypeptide, DNA molecules encoding the HIV-1 Vpr can be synthesized de novo. For example, complementary oligonucleotides can be synthesized and annealed to provide a double stranded DNA molecule encoding the polypeptide. The single stranded oligos can also be designed to include overhanging cohesive ends that allow the double stranded DNA molecules to be easily ligated. When designing the oligonucleotides, preferred features, such as codon optimization for the production host, and convenient restriction sites, can be engineered into the DNA molecule. In addition, if the subunit contains domains with identical or nearly identical amino acid sequences, different DNA sequences can be used to encode identical protein domains, allowing mutagenesis of each domain separately.

2. Use of Naturally Occurring DNA to Encode HIV-1 Vpr.

Alternatively, DNA sequences may be selected from naturally occurring genes that encode monomeric subunits of a trimeric protein complex. If necessary, the naturally occurring genes can be further modified to suit the needs of the user. One of skill in the art will recognize that PCR and mutagenesis techniques can be used to manipulate a DNA sequence to add convenient restriction sites or to mutagenize a DNA sequence as desired. Detailed descriptions of PCR and mutagenesis techniques can be found, for example at Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, mutagenesis kits are commercially available.

3. Expression of Cloned Genes Encoding Monomers.

To obtain high level expression of a cloned gene, such as those DNA sequences that encode an HIV-1 Vpr polypeptide, one typically subclones the DNA sequence into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al., supra. Bacterial expression systems are available in, e.g., *E. coli, Bacillus* sp., and *Salmonella* (Palva et al, *Gene* 22:229-235 (1983); Mosbach et al., *Nature* 302:543-545 (1983)). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the HIV-1 Vpr polypeptide encoding nucleic acid in host cells. A typical expression cassette thus contains a promoter operably linked to the nucleic acid sequence encoding a monomeric subunit and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a monomeric subunit encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of monomeric subunit protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al, supra). It is only necessary that the particular genetic engineering procedure used be capable of successfully introducing at least one gene into the host cell capable of expressing the HIV-1 Vpr polypeptide.

After the expression vector is introduced into the cells, the transfected cells are cultured under conditions favoring expression of the HIV-1 Vpr polypeptide, which is recovered from the culture using standard techniques identified below.

B. Purification of Expressed Proteins.

Polypeptides comprising HIV-1 Vpr protein and/or fragments thereof can be purified from any suitable expression system. The HIV-1 Vpr polypeptide may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al, supra).

1. Purification of HIV-1 Vpr Polypeptides from Recombinant Bacteria

Recombinant HIV-1 Vpr polypeptides can be expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the HIV-1 Vpr polypeptides from inclusion bodies. For example, purification of inclusion bodies typically involves the extraction, separation and/or purification of inclusion bodies by disruption of bacterial cells. The cell suspension can be lysed using 2-3 passages through a French Press; homogenized using a Polytron (Brinkman Instruments); disrupted enzymatically, e.g., by using lysozyme; or sonicated on ice. Alternate methods of lysing bacteria are apparent to those of skill in the art (see, e.g., Sambrook et al., supra; Ausubel et al, supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity.

Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. One of skill in the art will recognize that optimal conditions for renaturation must be chosen for each protein. For example, if a protein is soluble only at low pH, renaturation can be done at low pH. Renaturation conditions can thus be adjusted for proteins with different solubility characteristics i.e., proteins that are soluble at neutral pH can be renatured at neutral pH. Monomers are separated from other bacterial proteins by standard separation techniques.

2. Standard Protein Separation Techniques for Purifying HIV-1 Vpr Polypeptides a) Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

b) Size Differential Filtration

The molecular weight of the HIV-1 Vpr polypeptides can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

c) Column Chromatography

The HIV-1 Vpr polypeptides can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

IV. Preparation of Antibodies to the HIV-1 Vpr Polypeptide

Methods of producing polyclonal and monoclonal antibodies that react specifically with an HIV-1 Vpr polypeptide are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

Methods of production of polyclonal antibodies are known to those of skill in the art. An inbred strain of mice (e.g., BALB/C mice) or rabbits is immunized with the protein (i.e., immunogen) using a standard adjuvant, such as Freund's adjuvant, and a standard immunization protocol. The animal's immune response to the immunogen preparation is monitored by taking test bleeds and determining the titer of reactivity to the protein. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-HIV-1 Vpr proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a Vpr domain, can also be made, by subtracting out antibodies directed against other parts of the protein.

Once the specific antibodies against the HIV-1 Vpr polypeptide are available, the antibodies can be sequenced, or can be manipulated so as create chimeric or humanized antibodies. Alternatively, Vpr specific antibodies of the invention may be used to detect HIV-1 Vpr by a variety of immunoassay methods. For a review of immunological and immunoassay procedures, see *Basic and Clinical Immunology* (Stites & Terr eds., 7th ed. 1991).

V. Characterization of Monoclonal Antibodies

A. Isotype Determination

Mammalian immunoglobins have been classified into five primary classes (IgG, IgM, IgA, IgD and IgE) according to differences in their heavy chain polypeptides. Several of these classes can be further divided into subclasses, e.g., $IgG_1$, $IgG_2$, $IgG_3$, $IgG_4$, $IgA_1$, and $IgA_2$. These classes can be identified based on their reaction to antisera. Similarly, mammalian light chain constant regions can be assigned to one of two clearly distinct isotypes based on their amino acid sequence and reactions to different antisera. These isotypes are called δ (kappa) and λ (lambda).

Because the biological functions and biochemical characteristics of classes and isotypes differ, distinguishing the classes and isotypes of an immunoglobulin molecule is critical. Although any immunoaffinity method known in the art for can be used to determine antibody isotypes. The following provides an example of isotyping using an ELISA to determine the isotype of mouse antibodies.

For the ELISA assay, anti-mouse immunoglobulin antibodies are coated onto each well of a 96-well microtiter plate that serves as a solid support. Sample mouse immunoglobulins in solution are added and captured by the anti-mouse antibodies. Specific anti-mouse isotyping antibodies are then introduced and allowed to bind to the mouse-anti-mouse antibody complex. Finally, an enzyme-tagged antibody that reacts specifically with the anti-isotyping antibodies is added, which, together with a calorimetric substrate, indicate the immunoglobulin isotype of the sample. Antibody isotyping is well known in the art and kits are commercially available (e.g., isotyping kits such as the Isodetect kit are available from Stratagene, La Jolla, Calif.).

B. Epitope Mapping and Competitive Binding Assay

Regions of a given polypeptide that include an epitope can be identified using any number of epitope mapping techniques known in the art (see e.g., Epitope Mapping Protocols in Methods in Molecular Biology, Vol. 66 (Glenn E. Morris, ed., 1996) Humana Press, Totowa, N.J.) Methods for epitope mapping may include solving the crystal structure of an antibody-antigen complex or may involve analysis of vast libraries of random peptide sequences. However, the most convenient methods typically involve synthetic peptide based assays and competition assays.

Linear epitopes may be determined by synthesizing large numbers of peptides corresponding to portions of a protein molecule such as Vpr, on solid supports, and then reacting the peptides with antibodies while the peptides are attached to the supports. In this method, a set of overlapping peptides is synthesized, each corresponding to a small linear sequence of the antigen and arrayed on a solid phase. The panel of solid phase peptides is then probed with test antibodies and bound antibody is detected using enzyme-labeled secondary antibody. Methods for mapping linear epitopes are known in the art (see, e.g., Harlow and Lane, supra).

Alternatively, antigenic epitopes can be mapped by competition assay. Competition assay is a widely used method for determining if two antibodies are able to bind independently to the same protein antigen or whether their binding sites on the same protein overlap in such a way that both are not able to bind to the antigen at the same time.

Any method known for conducting a competition assay may be used to determine if a monoclonal antibody binds the same epitope as the 9F12 or 10F2 antibodies of the invention. For example, an ELISA format may be used. In ELISA the competition assay is initiated by first immobilizing the antigen (e.g., Vpr) on a solid substrate such as a 96 well plate. All antibodies to be used in the competition assay are then tested in direct binding assays to make certain that they are capable of binding the immobilized antigen. Direct binding assays are known in the art (see e.g., Harlow and Lane, supra). Those antibodies that bind the immobilized antigen in a direct binding assay can be used in the competition assay.

The competition assay is carried out wherein either the characterized antibody (e.g., 9F12 or 10F2 antibodies) or the test antibodies are labeled. In one aspect a label may permit a colorometric enzyme reaction to take place to reveal the presence of the labeled antibody. However, any convenient label may be used. If a colorometric assay is used, the label may be either indirectly or directly attached to the antibody. For example, an indirect label may be a biotin label that subsequently can be bound with a streptavidin peroxidase conjugate to reveal the presence of the antibody. Alternatively, the labeled antibody could be directly labeled with the peroxidase, or the antibody could be bound by a secondary antibody to which an enzyme is conjugated.

In one method of performing an ELISA based competition assay, the characterized antibody is left unlabeled. The characterized antibody is bound in the first step to the immobilized antigen. After the unlabeled characterized antibody has had sufficient time to bind the immobilized antigen, labeled test antibodies are added to the solution and allowed to compete for antigen binding in the presence of the unlabeled characterized antibody. After the test antibody has been given sufficient time to bind to the immobilized antigen (if it can do so), the wells containing the antibodies and antigen are washed to remove all the unbound antibodies, and signal from the label is measured.

If signal from the label is detected in the well after the wash step, then the test antibody binds a different epitope than the unlabeled characterized antibody. Alternatively, if no signal is detected, then the labeled test antibody binds the same epitope as the unlabeled characterized antibody. Similarly, the competition assay may be carried out with an unlabeled test antibody and a labeled characterized antibody. Competition assays are known in the art (see e.g., Harlow and Lane, supra).

C. Humanized Antibodies and Chimeric Antibodies

Techniques for humanizing antibodies involve selecting the complementarity determining regions (CDRs), i.e., the antigen binding loops, from a donor monoclonal antibody, and grafting them onto a human antibody framework of known three dimensional structure (see, e.g., WO98/45322; WO 87/02671; U.S. Pat. No. 5,859,205; U.S. Pat. No. 5,585,089; U.S. Pat. No. 4,816,567; EP Patent Application 0173494; Jones, et al. (1986) *Nature* 321:522; Verhoeyen, et al., (1988) *Science* 239:1534 Riechmann, et al. (1988) *Nature* 332:323; and Winter & Milstein, (1991) *Nature* 349:293).

The positions of the CDR's and hence the positions of the framework regions of the human heavy chain and light chains are determined using definitions that are standard in the art. For example, framework regions and antigen binding loop regions may be identified using a number of antigen binding loop definitions such as those by Kabat, Chothia, IMGT (Ruiz, et al., *Nucleic Acids Res.* 28:219-221 (2000); and Lefranc, *Nucl. Acids Res.* 29:207-9 (2001)), AbM (Martin et al, *Proc. Natl Acad. Sci. USA,* 86:9268-9272, (1989); Martin et al, *Methods Enzymol.* 203:121-153 (1991); Pedersen et al, *Immunomethods* 1:126 (1992); and Rees et al, In Sternberg M. J. E. (ed.), Protein Structure Prediction. Oxford University Press, Oxford, 141-172, (1996)), and contact (MacCallum et al., *J. of Mol. Biol.* 262:732-745 (1996)).

Human framework sequences can be obtained by the skilled artisan using well known techniques, e.g., using phage display libraries (see, e.g., Sastry et al, *Proc Natl Acad Sci USA* 86:5728-5732, 1989; McCafferty et al, *Nature* 348:552-554, 1990; Marks et al., *J Mol Biol* 222:581-597, 1991; Clackson et al, *Nature* 352:624-628, 1991; and Barbas et al., *Proc Acad Sci USA* 88:7978-7982, 1991) to isolate human $V_H$ and $V_L$ sequences, for example, corresponding to the B-cell repertoire of one or more individuals. The sequences are determined using standard technology.

$V_H$ and $V_L$ amino acid sequences are then aligned with a donor antibody, e.g., the antibody with the idiotype which specifically binds to the anti-idiotypic antibody used for screening, to select frameworks for humanizing the donor antibody. In brief, the heavy and light chain variable sequences of a donor antibody of interest, e.g., the murine monoclonal antibody 9F12 or 10F2, are aligned with uncharacterized human heavy and light chain sequences using e.g., the Abcheck software, e.g., available at http://www.bioinf.org.uk/abs/ (e.g., Martin, A. C. R. (1996) Accessing the Kabat antibody sequence database by computer. PROTEINS: Structure, Function and Genetics, 25, 130-133). The software aligns the provided sequence to a consensus sequence to map it to the Kabat numbering system. In an additional step, the aligned sequence is scanned against the Kabat database. The human sequences that have sequence identity of at least about 70% or greater are selected for candidate framework sequences for humanization. It is known that the function of an antibody is dependent on its three dimensional structure, and that amino acid substitutions can change the three-dimensional structure of an antibody. However, the antigen binding affinity of a humanized antibody can be increased by mutagenesis based upon molecular modeling (Riechmann, L. et al., Nature 332:323-227 (1998); Queen, C. et al., Proc. Natl. Acad. Sci. USA 6:10029-20033 (1989)). Thus, sequences selected for humanization are analyzed to determine important framework residues that can be backmutated to the donor sequence to obtain stable antibodies that bind to the same epitope as the donor antibody with a comparable affinity.

Chimeric antibodies are distinguished from humanized antibodies primarily in that the framework region is not derived from a human framework. Chimeric antibodies may be constructed by methods similar to those described above for the production of humanized antibodies.

D. Labeled Antibodies

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 dyes, fluorescein isothiocyanate, Texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The procedure for attaching an effector molecule to an antibody will vary according to the chemical structure of the moiety to be attached to the antibody. Polypeptides typically contain a variety of functional groups; e.g., carboxylic acid (COOH), free amine (—NH2) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

E. Detecting Antibody-Antigen Complex in a Sample

Once produced, the HIV-1 Vpr antibodies may be used in virtually any assay format that employs antibodies to detect antigens. Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules, as discussed in detail above. Assays which amplify the signals from the immune complex are also known; examples of which are assays which utilize biotin and avidin, and enzyme-labeled and mediated immunoassays, such as ELISA assays.

1. ELISA

HIV-1 Vpr may be used as an antigen in immunoassays such as enzyme-linked immunosorbent assays (ELISA), or in any antibody binding assays or procedures known in the art for the detection of anti-Vpr antibodies. Conversely, the 9F12 and 10F2 antibodies of the invention are useful for the detection of HIV-1 Vpr in biological fluids using any number of immunological assay methods known in the art, including ELISA (see, e.g. Ausubel et al. supra).

In ELISA assays, the biological fluid to be tested for the presence of Vpr is immobilized onto a selected surface, for example, a surface capable of binding proteins, such as the wells of a polystyrene microtiter plate. The solid support is reacted with the HIV-1 Vpr antigen, under suitable binding conditions such that the molecules are sufficiently immobilized to the support. Sometimes, immobilization to the support can be enhanced by first coupling the antigen and/or antibody to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) Bioconjugate Chem. 3:2-13; Hashida et al. (1984) J. Appl. Biochem. 6:56-63; and Anjaneyulu and Staros (1987) International J. of Peptide and Protein Res. 30:117-124.

After washing to remove incompletely adsorbed antigens, a nonspecific protein such as a solution of bovine serum albumin (BSA) that is known to be antigenically neutral with respect to the test sample may be bound to the selected surface. This allows for blocking of nonspecific adsorption sites on the immobilizing surface and thus reduces the background caused by nonspecific bindings of antisera onto the surface.

The immobilizing surface is then contacted with anti-Vpr antibodies of the invention, in a manner conducive to immune complex (antigen/antibody) formation. The mixture is then allowed to incubate for from 2 to 24 hours, at temperatures such as of the order of about 25° C. to 37° C. Following incubation, the anti-Vpr antibody-contacted surface is washed to remove non-immunocomplexed material. The washing procedure may include washing with a solution, such as PBS/Tween or a borate buffer.

Following formation of specific immunocomplexes between the anti-Vpr antibody and the affixed test sample, and subsequent washing, the occurrence, and even amount, of immunocomplex formation may be determined by subjecting the immunocomplex to a second antibody having specificity for the anti-Vpr antibody, as is known in the art. To provide detecting means, the second antibody may have an associated activity such as an enzymatic activity that will generate, for example, a color development upon incubating with an appropriate chromogenic substrate. Quantification may then be achieved by measuring the degree of color generation using, for example, a spectrophotometer.

2. Immunoaffinity Capillary Electrophoresis (ICE)

Capillary electrophoresis (CE) is a separation technique based on the differential migration of charged particles in an electric field (see e.g. Ausubel et al. supra). Basically, the method involves filling a thin capillary (20-100 μm internal diameter) with an electrolyte that provides a medium in which analytes can migrate through. A sample is introduced at one end of the CE unit. An electric field, typically of 100-400 μA constant current, is applied across the capillary to facilitate analyte species migration according to their electrophoretic mobility. The analyte species pass a detector as they migrate (usually UV or fluorescence) at or near the end of the capillary.

Capillary electrophoresis can be adapted to function in combination with immunoaffinity separation techniques to provide a sensitive method for obtaining reliable and reproducible analytical results for extremely small biological samples. Immunocapillary electrophoresis, which may also be known as immunoaffinity capillary electrophoresis or ICE, is essentially a modified immunoaffinity method that uses an electric field for elution of an antigen from an immunoaffinity column.

In an exemplary embodiment, an anti-Vpr antibody of the invention is immobilized to the internal wall of the first 5-cm of a 100-cm fused silica capillary. There are a large number of methods for covalently attaching antibodies to a solid phase. For example, depending on the isotype, antibodies can be coupled to protein A or protein G beads. Alternatively, antibodies can be coupled to beads that have been chemically modified to have active groups that will covalently bind the antibody. In a preferred embodiment FAb fragments are directly attached via their free thiol groups to thiol groups derivatized directly into the surface chemistry of the internal walls of the capillary as described in T. M. Phillips and P. Smith (2003) Biomed. Chromatogr. 17(2-3):182-187, and in T. M. Phillips (2001) J Biochem Biophys Methods. October 30; 49(1-3):253-62 each of which is herein incorporated by reference.

Samples of biological fluid for of testing are labeled with a dye that can be detected by the detection system, for example a red laser dye that can be detected using laser-induced fluorescence which is known in the art. After the sample is labeled, an aliquot of the labeled biological fluid is introduced into the capillary by vacuum injection. The labeled biological fluid is allowed direct contact with the immobilized antibody coating for at least 10 minutes to ensure that any Vpr antigen is bound by the immobilized anti-Vpr antibody.

Following incubation to bind the Vpr antigen to the immobilized antibody, non-bound material is purged by the application of a neutral pH phosphate buffer wash. The bound material is then recovered by electro-elution at 100-μA constant current with on-line laser-induced fluorescence detection.

EXAMPLES

The following examples are provided to illustrate, but not to limit the claimed invention.

Example 1

Isotype Determination and Epitope Mapping of 9F12 and 10F2 Vpr Antibodies

The 9F12 and 10F2 antibodies were characterized with respect to their isotype and with respect to the antigens on Vpr that they bind.

Isotype determination was made using an ELISA based format. Each well of a 96-well microtiter plate was coated with anti-mouse immunoglobulin antibodies. The 9F12 and 10F2 anti-Vpr antibodies were then added to separate, coated test wells and captured by the anti-mouse antibodies. Specific anti-mouse isotyping antibodies were then introduced and allowed to bind to the mouse-anti-mouse antibody complex. Finally, a peroxidase-tagged antibody that reacts specifically with the anti-isotyping antibodies was added, and colorimetric measurements indicated the immunoglobulin isotype of the sample.

Results of the isotyping experiments are shown in Table 1. Both the 9F12 and 10F2 antibodies are IgG1 kappa.

TABLE 1

|      | IgG1  | IgG2a | IgG2b | IgG3 | IgA   | IgM  | Igκ   | Igλ  | Type   |
|------|-------|-------|-------|------|-------|------|-------|------|--------|
| 9F12 | 1.795 | .022  | .01   | .055 | .014  | .012 | 1.514 | .015 | IgG1κ  |
| 10F2 | 2.112 | .024  | .022  | .021 | −.001 | .072 | 1.697 | .035 | IgGκ   |

Units are $OD_{450}$

To determine which epitopes of HIV-1 Vpr are bound by the 9F12 and 10F2 antibodies, epitope mapping experiments were carried out. Peptides were synthesized using a standard peptide synthesizer. The peptides were placed in 96 wells, and the test monoclonal antibodies ((F12 or 10F2) were added. Binding of antibody to peptide was detected by peroxidase-labeled secondary antibody.

Linear epitopes that are bound by the 9F12 and 10F2 antibodies were determined by synthesizing a series of overlapping peptides each corresponding to a small linear sequence of the Vpr polypeptide, on solid supports. The peptides were then reacted with antibodies while the peptides were still attached to the supports. The bound antibody was detected using enzyme-labeled secondary antibody.

The results of the epitope mapping experiments are summarized in Table 2. The data indicate that the 9F12 epitope maps to Vpr4-16, and the 10F2 epitope maps to 60-75, with possibly lesser reactivity to 45-60. The epitope may even extend on both sides of 60.

TABLE 2

|      | Vpr 1-96 | Vpr 1-40 | Vpr 1-20 | Vpr 1-15 | Vpr 30-45 | Vpr 1-8 | Vpr 1-8 $P^5 > N$ | Vpr 4-11 | Vpr 4-11 $P^{5,10} > N$ | Vpr 9-16 | Vpr 47-96 | Vpr 52-96 | Vpr 45-60 | Vpr 60-75 |
|------|----------|----------|----------|----------|-----------|---------|-------------------|----------|-------------------------|----------|-----------|-----------|-----------|-----------|
| 9F12 | +++      | +++      | +++      | +++      |           | +++     | +++               | +++      | +++++                   |          |           |           |           |           |
| 10F2 | +++      |          |          |          | +         |         |                   |          |                         |          | ++        | ++        | ++        | +++++     |

+ is indicative of weak binding,
+++++ is indicative of strong binding;
$P^{XX} > N$ means that proline at these amino acid positions is mutated to asparagine in these peptides.

Example 2

Immunoaffinity Capillary Electrophoresis Assay for the Detection of Vpr

Figure 1:
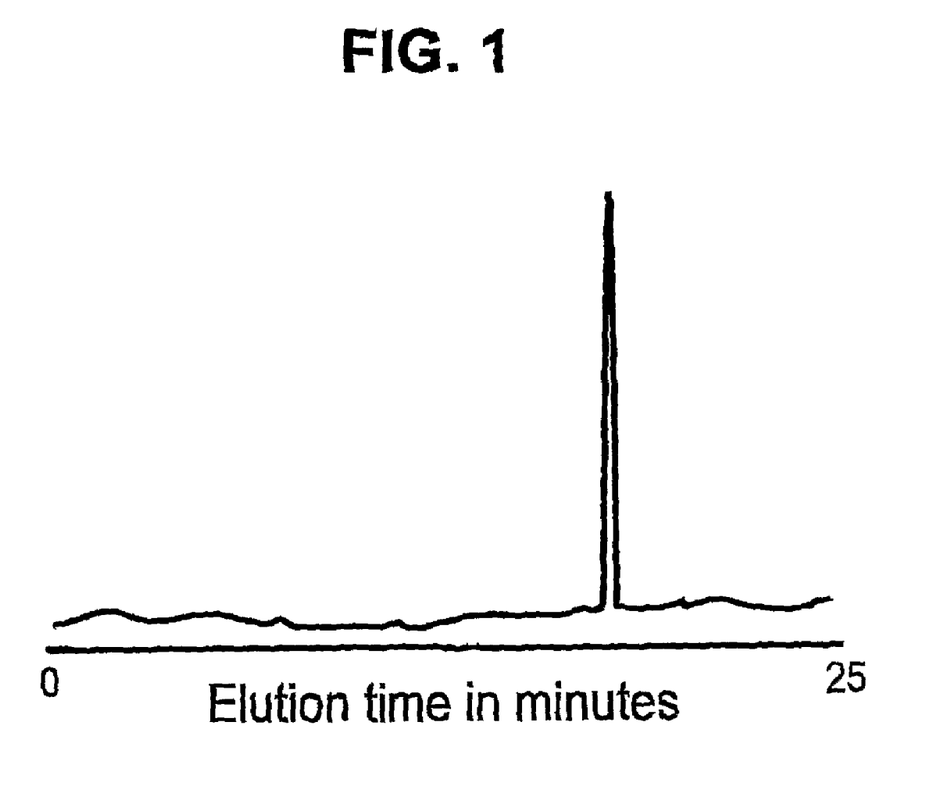
FIG. 1 shows an electropherogram result of immunoaffinity capillary electrophoresis of a sample containing Vpr versus immobilized 9F12 anti-Vpr antibody of the invention.

Immunoaffinity capillary electrophoresis (ICE) was used to detect and quantitate HIV-1 Vpr in a sample. 9F12 anti-Vpr antibody was immobilized on the internal wall of the first 5-cm of a 100-cm fused silica capillary. Samples containing Vpr were labeled with a red laser dye (AlexaFluor633 from Molecular Probes, Oregon) and 50-nanoliters of the labeled sample was introduced into the capillary by vacuum injection. The injected sample was allowed direct contact with the immobilized antibody coating for 10 minutes. Non-bound material was purged by the application of a neutral pH phosphate buffer wash, and the bound material was recovered by electro-elution in phosphate buffer at pH 1.5 for 25 minutes at 100-μA constant current with on-line LIF detection. FIG. 1 illustrates an electropherogram of Vpr showing the results of immunoaffinity capillary electrophoresis of a sample containing Vpr versus immobilized 9F12 anti-Vpr antibody of the invention.

Example 3

Measuring Vpr in the Plasma and Urine of Patients with HIV-1 Infection

Infectious HIV-1 in plasma and urine samples was rendered inactive by the addition of Panvirocide, which contains glutaraldehyde and three detergents, nonoxynol, Brij-23, NP-40. Patient samples were assayed for Vpr using the monoclonal antibody 9F12 in an immunocapillary electrophoresis assay as described in Example 1. The standard for calibration was synthetic Vpr 1-96 peptides, diluted in normal patient plasma.

Results of the experiments showed that among 4 healthy volunteers, all had <0.5 ng/ml Vpr in plasma. Among the 9 HIV-1 infected patients, median plasma Vpr concentration was 3 ng/ml, with a range from 1.3 to 171 ng/ml, and the median urine Vpr was 2 ng/ml, with a range of 0.1 to 34 ng/ml.

Example 4

Using Immunoaffinity Capillary Electrophoresis to Compare the Amount of HIV-1 Viral Protein R in the Sample to a Standardized Control to Determine Disease Progression or the Presence of Certain Complications Such as Neuropathy or Metabolic Syndrome Plasma, CSF and/or urine will be obtained from HIV-1 infected patients with a condition under study (e.g., dementia where CSF Vpr levels would be particularly important, metabolic syndrome, and nephropathy where urine Vpr levels would be particularly important) and from HIV-1 infected patients lacking the condition, but otherwise matched in appropriate ways (e.g. CD4 count and HIV-1 viral load). Vpr will be measured in these samples as outlined above, and the levels of Vpr in various biological fluids will be compared to patients with the condition and those without the condition. If Vpr levels are consistently higher in patients with the condition, then Vpr measurement may help in 1) diagnosis of the condition, 2) the development of new therapies targeted to reducing Vpr levels or antagonizing the effects of Vpr on host cells, and 3) monitoring the effect of Vpr-lowering therapies on Vpr levels.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Accession Nos. are incorporated herein by reference for all purposes.

What is claimed is:

1. A first antibody to a Human Immunodeficiency Virus (HIV)-1 viral protein R (Vpr) that competitively inhibits binding of a second antibody to the HIV-1 Vpr, wherein the second antibody is produced by the hybridoma cell line 9F12 as deposited under American Type Culture Collection patent deposit number PTA-5560, and wherein the first antibody comprises the six complementarity determining regions (CDRs) from the second antibody and is selected from the group consisting of a monoclonal antibody, a chimeric antibody, a humanized antibody, and a functional fragment thereof comprising the six CDRs from the second antibody.

2. The first antibody of claim 1, wherein the first antibody is a monoclonal antibody.

3. A humanized antibody to a Human Immunodeficiency Virus (HIV)-1 viral protein R (Vpr) or a functional fragment thereof comprising the six complementarity determining regions (CDRs) from the antibody produced by the hybridoma cell line 9F 12 as deposited under American Type Culture Collection patent deposit number PTA-5560.

4. A chimeric antibody to a Human Immunodeficiency Virus (HIV)-1 viral protein R (Vpr) or a functional fragment thereof comprising the six complementarity determining regions (CDRs) from the antibody produced by the hybridoma cell line 9F12 as deposited under American Type Culture Collection patent deposit number PTA-5560.

5. The first antibody of claim 1, conjugated to a detectable label.

6. An isolated hybridoma cell line 9F12 as deposited under American Type Culture Collection patent deposit number PTA-5560.

7. A method for detection of a Human Immunodeficiency Virus (HIV)-1 viral protein R (Vpr) in a sample, comprising the steps of:
   (i) contacting a sample with a first antibody to HIV-1 Vpr or a functional fragment thereof, wherein the first antibody or the functional fragment thereof comprises the six complementarity determining regions (CDRs) from the second antibody produced by hybridoma cell line 9F12 as deposited under American Type Culture Collection patent deposit number PTA-5560, and is capable of competitively inhibiting binding of the second antibody to the HIV-1 Vpr; and
   (ii) detecting a first antibody-Vpr complex in the sample.

8. The method of claim 7, further comprising the step of:
   (iii) quantitating the amount of the antibody-Vpr complex to determine the amount of HIV-1 Vpr in the sample.

9. The method of claim 7, wherein the sample is a biological fluid from a patient.

10. The method of claim 9, wherein the biological fluid is selected from the group consisting of serum and plasma.

11. The method of claim 7, wherein the first antibody is detectably labeled.

12. The method of claim 7, wherein the step of detecting is carried out using capillary electrophoresis.

13. The method of claim 12, wherein the capillary electrophoresis is immuno-capillary electrophoresis.

14. The method of claim 9, further comprising the steps of:
   (iii) quantitating the amount of the antibody-Vpr complex to determine the amount of HIV-1 Vpr in the sample; and
   (iv) comparing the amount of HIV-1 Vpr in the sample to a standardized control to determine HIV-1 disease progression of the patient.

15. The method of claim 9, further comprising the steps of:
   (iii) quantitating the amount of the antibody-Vpr complex to determine the amount of HIV-1 Vpr in the sample; and
   (iv) comparing the amount of HIV-1 Vpr in the sample to a standardized control to determine the presence of complications associated with HIV-1 infection in the patient.

16. The method of claim 15, wherein the complication is selected from the group consisting of neuropathy, dementia, metabolic syndrome, and nephropathy.

17. The first antibody of claim 1, wherein the first antibody further comprises a variable region of a heavy or light chain of the second antibody.

18. The first antibody of claim 1, wherein the first antibody further comprises the variable regions of heavy chain and light chain of the second antibody.

19. The first antibody of claim 17, wherein the first antibody is conjugated to a detectable label.

20. The first antibody of claim 1, wherein the first antibody is a humanized antibody.

21. The first antibody of claim 20, further comprising a variable region of a heavy or light chain of the second antibody.

22. The first antibody of claim 20, further comprising the variable regions of heavy chain and light chain of the second antibody.

23. The first antibody of claim 1, wherein the first antibody is a chimeric antibody.

24. The first antibody of claim 23, further comprising a variable region of a heavy or light chain of the second antibody.

25. The first antibody of claim 23, further comprising the variable regions from of heavy chain and light chain of the second antibody.

26. A monoclonal antibody to a Human Immunodeficiency Virus (HIV)-1 viral protein R (Vpr) or a functional fragment thereof comprising the six complementarity determining regions (CDRs) from the antibody produced by the hybridoma cell line 9F12 as deposited under American Type Culture Collection patent deposit number PTA-5560.

27. A monoclonal antibody produced by the hybridoma cell line 9F12 as deposited under American Type Culture Collection patent deposit number PTA-5560.

28. A method for detection of a Human Immunodeficiency Virus (HIV)-1 viral protein R (Vpr) comprising the steps of:
   (i) contacting a sample with the monoclonal antibody of claim 27; and
   (ii) detecting an antibody-Vpr complex in the sample.

29. The method of claim 28, wherein the monoclonal antibody is detectably labeled.

* * * * *